United States Patent
Cope et al.

(10) Patent No.: US 7,735,626 B2
(45) Date of Patent: Jun. 15, 2010

(54) APPARATUS, METHOD AND SYSTEM FOR HANDLING, POSITIONING, AND/OR AUTOMATICALLY ORIENTING OBJECTS

(75) Inventors: Jason Cope, Ankeny, IA (US); David Kurth, Grimes, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 295 days.

(21) Appl. No.: 11/939,380

(22) Filed: Nov. 13, 2007

(65) Prior Publication Data
US 2008/0131254 A1 Jun. 5, 2008

Related U.S. Application Data

(60) Provisional application No. 60/865,563, filed on Nov. 13, 2006, provisional application No. 60/865,554, filed on Nov. 13, 2006.

(51) Int. Cl.
*B65G 47/24* (2006.01)
(52) U.S. Cl. .................... 198/381; 198/690.1; 47/56; 111/178
(58) Field of Classification Search ........... 198/381, 198/690.1; 111/104, 177, 178, 199, 200; 47/56
See application file for complete search history.

(56) References Cited

U.S. PATENT DOCUMENTS

| | | | | |
|---|---|---|---|---|
| 2,675,942 | A | | 4/1954 | Vogelsang |
| 2,875,942 | A | * | 3/1959 | Wilson ................ 229/109 |
| 3,344,769 | A | * | 10/1967 | Williams ............... 118/69 |
| 3,636,486 | A | | 1/1972 | Ioffe et al. |
| 3,741,793 | A | * | 6/1973 | Simmons ............... 427/477 |
| 3,830,902 | A | * | 8/1974 | Barnes ................ 264/267 |
| 3,831,736 | A | * | 8/1974 | Barnes ................ 198/803.6 |
| 3,884,347 | A | | 5/1975 | Gallagher et al. |
| 3,930,212 | A | * | 12/1975 | Ioffe et al. ............... 198/381 |
| 3,991,704 | A | * | 11/1976 | Hulstein et al. ........... 118/684 |
| 4,238,658 | A | * | 12/1980 | Kalnin et al. ............. 219/603 |
| 4,278,625 | A | * | 7/1981 | Dedolph ................ 47/56 |
| 4,300,462 | A | * | 11/1981 | Wilkins et al. ............ 111/91 |

(Continued)

FOREIGN PATENT DOCUMENTS

EP 0 611 604 A2 8/1994

(Continued)

OTHER PUBLICATIONS

Search Report for co-pending PCT/US2007/084546 listing relevant art cited by the International Searching Authority.

(Continued)

*Primary Examiner*—James R Bidwell
(74) *Attorney, Agent, or Firm*—Alston & Bird LLP

(57) ABSTRACT

A method and apparatus for automatic positioning and/or orientation of an object. The method includes applying a substance or component to an object, or takes advantage of a substance or component already on or associated with an object. The substance or component has a characteristic that can be utilized to automatically attract the substance or component. That characteristic is used to position, move, and/or orient the object automatically, without requiring manual handling. The object can then be further processed or handled. In one embodiment, the substance or component is a magnetically active substance or component. The attraction can be actuated by a magnet.

30 Claims, 6 Drawing Sheets

U.S. PATENT DOCUMENTS

| | | | |
|---|---|---|---|
| 5,097,625 A * | 3/1992 | Kaneko et al. | 47/56 |
| 6,409,007 B1 | 6/2002 | Malon | |
| 7,043,070 B2 | 5/2006 | Viella | |
| 7,197,374 B2 | 3/2007 | Silverbrook et al. | |
| 7,207,485 B2 | 4/2007 | Silverbrook et al. | |

FOREIGN PATENT DOCUMENTS

| | | |
|---|---|---|
| GB | 2 293 744 | 4/1996 |

OTHER PUBLICATIONS

John W. K. Leung and K. K. Lai; *Performance analysis of automatic assembly systems with in-line parallel stations*; IMA Journal of Mathematics Applied in Business & Industry; 1997; pp. 1-22; vol. 8, No. 1.

Sangtong, et al.; *Serial Extraction of Endosperm Drillings (SEED)—A Method for Detecting Transgenes and Proteins in Single Viable Maize Kernels*; Plant Molecular Biology Reporter; Jun. 2001; pp. 151-158; vol. 19; 2001 International Society for Plant Molecular Biology.

* cited by examiner

APPARATUS, METHOD AND SYSTEM FOR HANDLING, POSITIONING, AND/OR AUTOMATICALLY ORIENTING OBJECTS

RELATION TO OTHER APPLICATIONS

This invention claims priority under 35 U.S.C. Section 119 to U.S. Provisional Applications No. 60/865,563 and No. 60/865,554, both filed Nov. 13, 2006, each of which is incorporated by reference in its entirety.

BACKGROUND OF THE INVENTION

The present invention relates to automated handling of objects, and particularly, automatic positioning and/or orienting them.

RELATED ART

A variety of situations exist where relatively small, discrete objects or parts need to be handled, positioned, and sometimes placed in a specific orientation.

A vast number of apparatus and methods have been developed over the years for sorting discrete objects, pieces, or components. For example, some sort on the basis of shape. Some sort on the basis of size. Some more complex systems even use such things as artificial or machine vision and sort on the basis of color or physical characteristics from image analysis.

Sorting or discriminating between objects involves certain technological and practical issues. Automatic handling and positioning of relatively small objects can include similar or additional issues.

Difficulties in automatic orientation of objects in automatic assembly processes have been widely discussed. See, e.g., J. W. K. LEUNG and K. K. LAI, "Performance analysis of automatic assembly systems with in-line parallel stations", IMA Journal of Management Mathematics 1997 8(1):1-22. For example, it can be quite advantageous to automatically orient parts in preparation for automatic assembly of the parts with other parts or components. A variety of computer-aided manufacturing systems have been proposed or developed toward those ends. Robotics and machine-vision-based systems are examples. See, e.g., U.S. Pat. No. 7,043,070.

It is common in automatic assembly that a part or subassembly of parts must be assembled to another part of subassembly of parts in a specific positional relationship. An example of automatic orientation is an automated vision system with robotic arm. It is calibrated to recognize orientation of both arm and object with computer vision and instruct the robotic arm to pick up the object and orient it to the correct orientation for the assembly process. As can be appreciated, such systems can be quite complex, expensive, and difficult to calibrate. See also, e.g., U.S. Pat. Nos. 6,409,007 and 7,197,374. These systems also require each part to be individually handled by the robot, which can be time-consuming and reduce throughput. It also can lead to errors.

Automated packaging can also benefit from automatic orientation of the objects to be packaged. See, e.g., U.S. Pat. No. 7,207,485. The packaging operation can many times be made more efficient if the objects to be packaged are in a consistent, known orientation.

Still further, a number of automated inspection or quality control systems can benefit from automatic and consistent pre-determined orientation in preparation for further operations to be conducted on the object. Calibration of the machine-vision or other automated inspection equipment can be less complex if the objects to be inspected are in a consistent, pre-determined orientation.

There is room for improvement in the art of automatic positioning and orientation of objects. In particular, there is room for improvement with respect to efficiency, cost, and complexity of such systems or approaches.

BRIEF SUMMARY OF THE INVENTION

An embodiment of the present invention comprises an apparatus, method, and system which improves over or solves problems or deficiencies in the state of the art.

Other embodiments of the present invention include an apparatus, method, or system which:

a. has the ability to not only handle and position relatively small objects but also, in certain cases, orient them in a predetermined way;

b. can handle relatively large quantities of objects;

c. can handle relatively large quantities of objects efficiently and economically;

d. can have substantial flexibility with respect to needed functions and applications;

e. can be used in a variety of applications, including but not limited to positioning of discrete, relatively small items for conducting processes on those items, or positioning small discrete items so that they can be then added to or combined with something else (e.g. assembled to another piece in a manufacturing or assembly process).

A method according to one embodiment of the invention applies a substance or component to an object, or takes advantage of a substance or component already on or associated with an object. The substance or component has a characteristic that can be utilized to automatically attract the substance or component. That characteristic is used to position, move, and/or orient the object automatically, without requiring manual handling. The object can then be further processed or handled. In one embodiment, the substance or component is a magnetically permeable or active (e.g. susceptible to magnetic fields) substance or component.

An apparatus according to an embodiment of the present invention includes a substance or component, as previously described, that is applied to one or more objects or is inherent or already associated with the object. An attraction means or device, having an actuation mechanism to take advantage of the characteristic, is adapted for operation to position and/or orient each object. In one embodiment, the substance or component is a magnetically active substance or component and the attraction means or device is a magnet.

DETAILED DESCRIPTION OF EXEMPLARY EMBODIMENTS

Figure 1A:
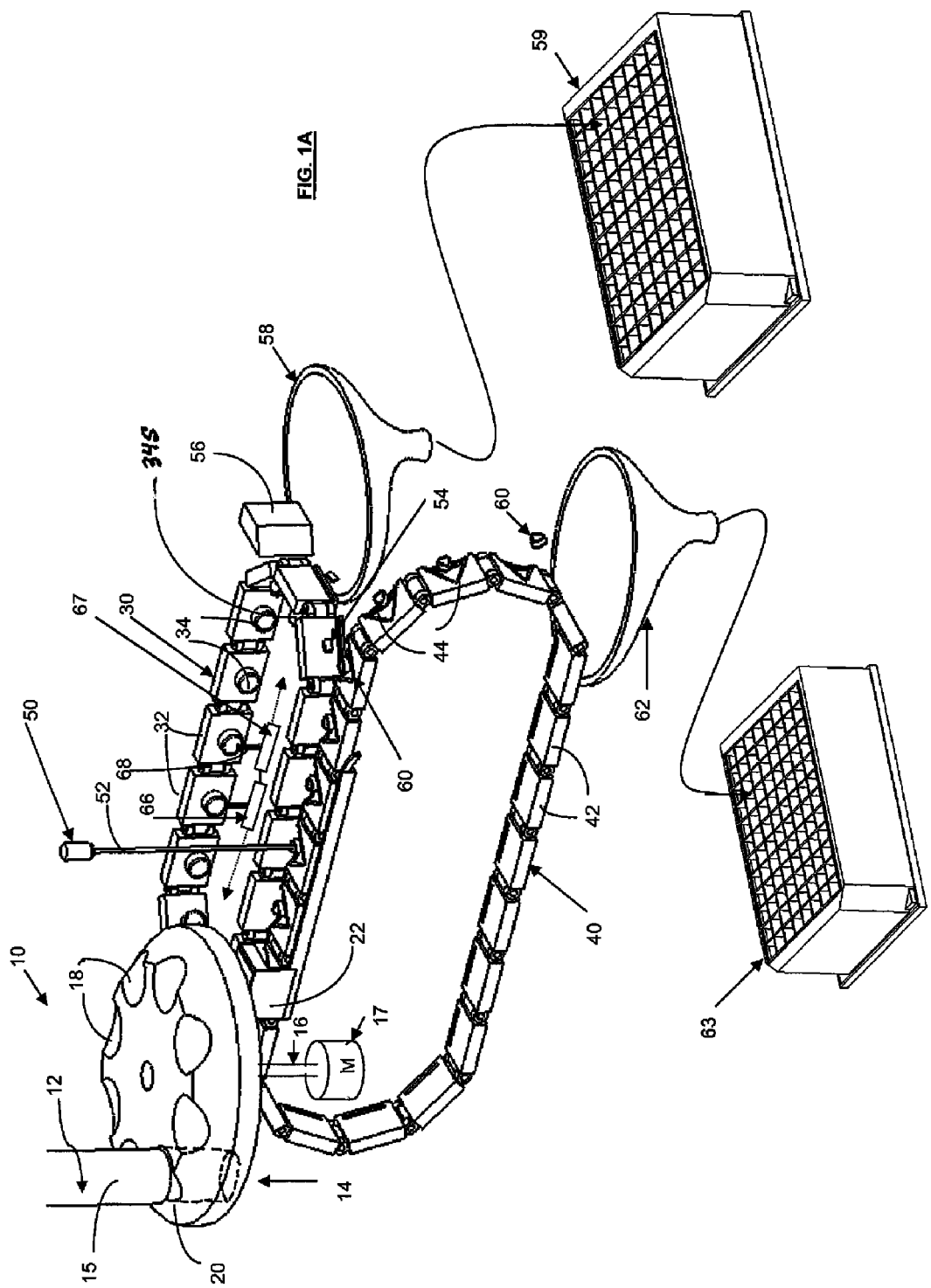
FIG. 1A is a perspective view of an exemplary embodiment according to one aspect of the present invention which magnetically orients a serial succession of individual objects, here seed, relative to a laser beam to then perform an operation on the object, here to non-lethally sever and collect a sample from each seed.

For a better understanding of the invention, examples of how the invention can be practiced will now be described in detail. It is to be understood that these are but a few forms the invention can take and do not limit the invention.

This description will include frequent reference to the accompanying drawings. Reference numerals and/or letters will be used to indicate certain parts and locations throughout the drawings. The same reference numerals will be used to indicate the same parts or locations unless otherwise indicated.

A. EMBODIMENT 1

FIGS. 1A and B

By referring to FIGS. 1A and B, a method, apparatus, and system according to one exemplary embodiment of the invention is shown. The goal is to position and orient a number of kernels of corn in a predetermined way so that a sample of each kernel from a consistent location on each kernel can be obtained.

In this case the objects to be positioned and oriented are corn kernels. A substance is applied to each kernel prior to automatic orientation. In this example, the substance is a magnetically active paint.

The iron-based paint covering the crown of each seed and magnets 34 are utilized to automatically position and orient each singulated seed relative to a laser beam. An example of such iron-based paint is available commercially, namely Krylon® Magnetic Spray Paint (product # 3151, 13 oz. aerosol spray can from The Sherwin-Williams Co., Krylon Products Group, Cleveland, Ohio USA). It can be sprayed onto the exterior of ear of corn 1.

By empirical study, the amount of paint relative to the strength of the magnet can be established to create consistent positioning and orientation of seed. After the paint dries on ear 1, the ear is shelled by conventional means. One example is by an automatic sheller (e.g., Model SCS-2 Sheller from Agriculex Inc., Guelph, Ontario CANADA).

While the kernels are on the cob, the iron-based paint is applied to the outer surface of the cob. This covers what is called the crown of each kernel. As the kernels are packed in abutment on the cob, the paint will tend not to seep or bleed much down the sides of the kernel (see FIG. 1B).

Figure 1B:
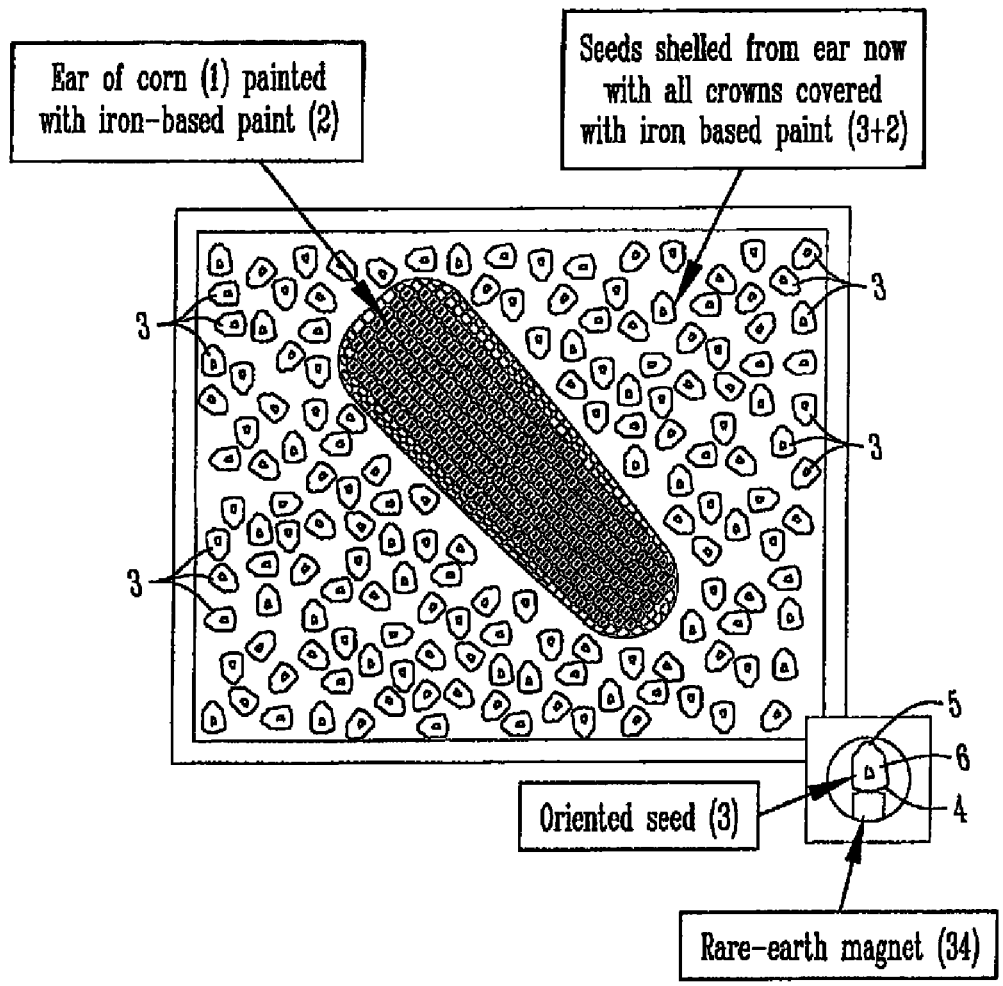
FIG. 1B illustrates an exemplary method of applying to seed on an ear of corn an iron-based paint so that the crown of each seed will be attracted to a magnet once shelled from the ear.

By conventional means, the ear of corn is shelled which non-destructively separates the kernels off their carrier (the cob) into discrete objects, resulting in a random set of individual kernels, each with iron-base paint on its crown (FIG. 1B).

The set of kernels of FIG. 1B are moved to a platform having a surface with a plurality of individual magnets at uniformly spaced positions under the platform (see FIG. 1A). By vibratory action or other means and methods, the kernels are distributed across the platform. The magnets will attract at least one kernel and hold it in position. In this particular example, because the iron-based paint is only on the crown, the crown will be attracted to the magnet and thus the opposite end of the kernel, the tip cap, will be pointed up. As shown in FIG. 1A, this methodology allows the random set of kernels to be automatically positioned in predetermined positions on the platform, as well as automatically oriented to a consistent tip cap up/crown down predetermined orientation.

Once in position, further processing can occur. For example, in one application it is desirable to have the tip caps all up and at a distal position from the platform so that they would be in position to have the seed crown removed by a blade, a sander, or other means. However, because each kernel is basically in a consistent orientation, an automated system can alternatively be configured to take a tissue sample from almost any part of the kernel, not only the crown, but other parts of the kernel. Alternatively, some other operation could be performed on each or selected seed. A few non-limiting examples include applying some other substance to a selected part of the seed (e.g. antifungal agent, insecticide, fertilizer, sealant), encasing or packaging each seed or a part thereof, or marking each (or selected) seed. Other examples are possible.

More specifically, the shelled painted seed is put into a seed singulator. Buffer wheel 14 rotates at a predetermined speed correlated to the speeds of conveyor 30 and conveyor 40. A motor 17 is connected to buffer wheel 14 by axel 16. Buffer wheel 14 has individual and equally spaced wells 18. Each well has an opening 20 at its bottom big enough for a seed to fall through. Wells 18 are dimensioned to capture one seed 3 at a time as individual seeds are delivered from the seed singulator. The motors, wheels, conveyor 30, and conveyor 40 would operate in a complimentary fashion to buffer wheel 14 as follows.

A fixed, non-rotating plate (not shown but could be similar to plate 21 of FIG. 1C), would exist underneath buffer wheel 14 and have a single opening in correspondence with chute 22. Seed in each well or receiver 18 of buffer wheel 14 (which would rotate on top of the fixed, non-rotating plate) would thus be held in that position until the respective opening 20 of its well or receiver 18 comes into correspondence to chute 22. The seed in that well 18 in correspondence with chute 22 would fall through a hole 20 in bottom of well or receiver 18, and the hole in the fixed, non-rotating plate. Chute 22 would direct the seed into a V-shaped depression in a link 42 of conveyor belt 40. Each link 32 of conveyor belt 30 includes a magnet 34 on its back side. Conveyor belts 30 and 40 would both turn clockwise and concurrently in such a manner that a single link 32 would remain adjacent a corresponding single link 42. As can be appreciated, the timing would be set up to drop each seed 3 through chute 22 just ahead of its corresponding magnet 34 on a link 32 so seed 3 reaches the magnet 34 with precise timing.

In this manner, each seed 3 with iron-based paint that falls into a V-depression in a link 42 would be oriented such that the painted crown of seed 3 would be attracted and brought into abutment with link 32 because of the presence of magnet 34 on the other side of link 32. This would, conversely, orient the tip cap of each corn kernel 3 away from link 32.

As shown in FIG. 1A, each oriented seed 3 would proceed past laser 50. Laser 50 would be positioned and configured so that its laser beam 52 would sever a piece or clip 54 from each seed 3 (here it would slice off a sliver from the seed crown). The V-depression in link 42 would retain the now separated cut seed 60 in position as it moves to the right in FIG. 1A. The clip 54 (which includes iron-based paint) would remain attracted and adhered to link 32 as conveyors 30 and 40 separate.

A scraper 56 could scrape or force each clip 54 from its corresponding link 32 and clip 54 would fall into sample collecting funnel 58. Instead of a scraper, a brush or brushes could be used to wipe clips 54 from belt 30. Alternatively, electromagnets could be used, and turned off to drop clips 54 into funnel 58. In another embodiment, the magnets 34 could momentarily separate from link 32 at a position directly above the sample collecting funnel 58 which would temporarily release the magnetic field and drop clips 54 (see reference numeral 34S, which is intended to diagrammatically illustrate the magnet 34 at that point being tilted away and down to release the sample 54). Optionally, vacuum could be used to remove clips 54 from belt 30. A focused burst of air could be utilized in order to collect the clip from the wheel into a funnel or other such vessel.

As shown diagrammatically in dashed lines, sample collection funnel 58 would have a tube that would direct a first clip 54 into a designated well in sample well or plate 59. Each clip 54 would be directed to a separate well in well plate 59. The sample plate 59 could be moved so that the next well is under the tube as the next clip 54 drops, and so on, until all clips are in a respective well or the tray is full.

Correspondingly, each cut seed 60 would travel to the right on conveyor 40 until, by gravity, it would fall out of its link 42 into seed collection funnel 62. By appropriate components or procedures, each cut seed 60 would be directed to a well of well plate 63.

As can be appreciated, corresponding clips 54 and cut seed 60 would be placed in analogous wells in well plates 59 and 63 so that laboratory results from clips 54 can be matched up with the relating seed at a later time.

As can be appreciated, each conveyor 30 and 40 could be synchronized by appropriate gearing. FIG. 1A does illustrate that each magnet 34 could be held adjacent to a corresponding link 32 by a post 68 that extends from a link 67 of a conveyor belt 66 that is positioned underneath and is basically identical in size to conveyor belt 30. Each post 68 could be attached to its link 67 by a spring. Some type of object or mechanical part could deflect and tilt each post 68 away from belt 30 at position 34S to move the corresponding magnet away, as previously described, to cause clip 54 to drop. Once post 68 is past position 34S, it would spring back to position where its magnet 34 would be held against or closely adjacent to its link 32. Conveyor 66 could also be synchronized with belts 30 and 40 via appropriate gearing or other methods.

Magnets 34 would attract the crown portion of each seed 3 because of the high magnetic activity of the iron in the iron-based paint. An example of magnet 34 is a neodymium rare-earth magnet. These tend to produce relatively strong magnetic fields for their size. Empirical testing can provide the correct magnetic strength of magnets 34 for a given iron-based paint and a given size and thickness of links 32 of conveyor 30.

Figure 1C:
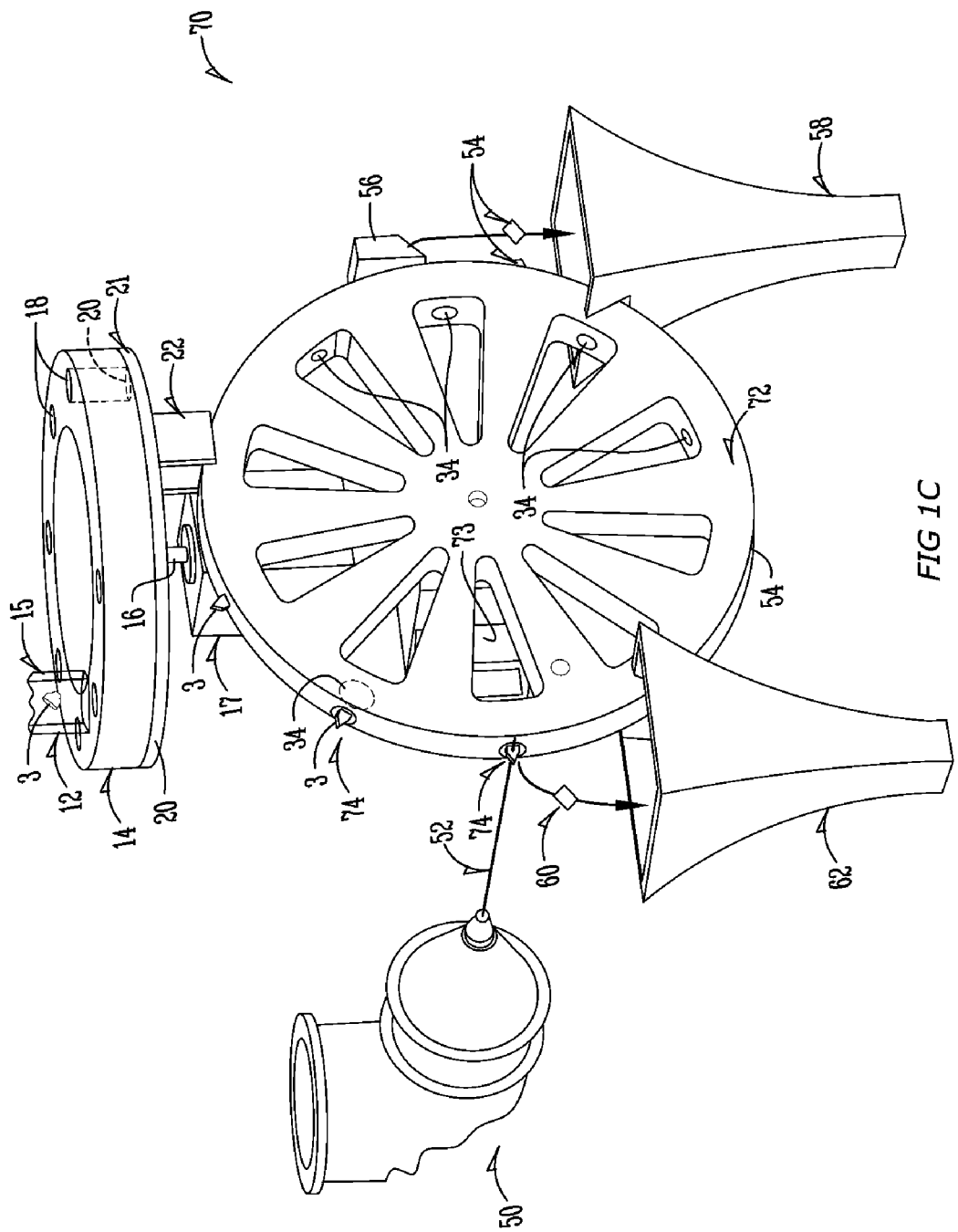
FIG. 1C is an alternative exemplary embodiment to that of FIG. 1A.

The size of one example of magnet 34 is illustrated in FIGS. 1A-C (see particularly the isolated illustration in FIG. 1B, showing a magnet 34 and a single seed 3 of corn). It is preferable that the size of magnet 34 be as small as possible but provide sufficient magnetic field strength to attract and hold the iron-based paint located on the crown of a seed 3 in the position and orientation shown in FIGS. 1A-C, included as it moves in the systems of FIGS. 1A and 1C. The specifications for such a magnet might include, but are not limited to, a neodymium rare-earth magnet in a variety of shapes which range from 1/16" to 2" in length or diameter, from 1/16" to 1" in thickness, from 0.5 lbs. to 175 lbs holding force, and from a 11.5-14.5 Kilogauss surface field (e.g. rare-earth magnets from CMS Magnetics located at 1108 Summit Ave., Suite 8, Plano, Tex. 75074).

As previously described, in the embodiment of FIG. 1A, magnets 34 are fixedly mounted to posts 68 or other structure that hold against or in close proximity to and move synchronously magnets 34 relative to corresponding links 32 of conveyor belt 30, except at location 34S. Selection of the components is such that magnets will hold seed with magnetic paint or the clips with magnetic paint to the opposite side of the link until location 34S, where structure would move the magnet 34 at location 34S away enough that the magnetic attraction would attenuate enough that the clip 54 would drop by gravity from its link 32. Alternatively, magnets 34 might be attached by adhesive, interference fit, or other methods to the inside of each link 32 of conveyor belt 30 and be powerful enough to attract the iron-based paint through link 32, and use scraper 56 to remove clips 54, or some other method.

As indicated in FIG. 1A, laser beam 52 would cut off essentially just the crown of each seed 3. Because the seed 3 is consistently oriented, and because laser beam 52 can create a very clean and thin cut (a very fine kerf of approximately 0.003" to 0.007"), system 10 allows severing of a clip 54 of sufficient quantity that it can be utilized for conventional laboratory analytical procedures to test for genetic constituents, seed components, etc., while leaving cut seed 60 intact and with a relatively high propensity to germinate. Thus, system 10 has been shown to be a non-lethal way to get sample tissue from corn seed without being substantially detrimental to the germination rate of the seed.

An example of a laser 50 that can be used is a sealed carbon dioxide ($CO_2$) laser. One example is a water-cooled Fire Star 201 Series $CO_2$ 200 watt laser, Model No. FSF201SB from Synrad, Inc. of Mukilteo, Wash. USA. A beam delivery system transfers the raw laser beam from the sealed laser and focuses it at the location the seed is to be cut. Such a beam delivery system can be purchased from Haas Laser Technologies Inc.; a 1.25 inch series beam delivery system with a 5 inch focal lens. Cut rate in this embodiment is 2 to 3 rpm and usually results in separation of the sample with one pass of the laser beam. The system could be set to allow two passes. The beam does produce some heat which tends to cauterize the kerf.

As can be appreciated by those skilled in the art, in this exemplary embodiment used for plant advancement experiments, it is normally preferable that the amount of sample taken from the seed 3 have as little detrimental impact on germination potential as possible. This is also preferable regarding the type of method of separating the sample from the seed. Also, it is preferable that the amount of sample removed be enough for meaningful results from any anticipated analytical procedures.

The location of the sample can be adjusted. In this example, the application of iron-based paint to the crowns and the geometry of the conveyors relative to the laser beam results in the removal of the crown, which contains endosperm. The laser beam could be adjusted to instead remove the tip cap which can be an important structure for certain analysis. However removing the tip cap would likely prevent subsequent germination of the seed. Also, the iron-based paint could optionally be applied to other locations of the seed so that each seed would be oriented in other ways and, thus, samples could come from other areas of the seed, if desired. However, in this example, the goal is to sample the endosperm. It is preferable that the amount of sample be such that the ratio of pericarp to endosperm is as small as possible if using the sample for genetic analysis.

The size of clips or cut samples 54 can vary according to design. In the present example, the average size of clip 54 taken from maize seeds was between 10 and 15 mg. For some purposes, an average size of about 20 mg was preferred. However, as stated above, a seed could be divided into almost any proportion of two parts, depending on the laser cut. One of skill in the art will recognize that the size of sample taken from a given seed will vary based on the type of seed being sampled, the size of seed being sampled, and the intended analysis to be performed on the sample that is obtained. However, it should be understood that depending on the species of seed, larger sample sizes may impact germination.

As can be appreciated, timing of buffer wheel 14 and movement of conveyor belts 30 and 40 (and conveyor belt 66, if used) can be coordinated by a variety of methods, including selection and adjustment of the corresponding motors or, in a more sophisticated system, using a digital programmable logic controller or other analogous means and methods.

Once clips 54 and cut seed 60 have been properly indexed in index trays 59 and 63, trays 59 and 63 can be taken to a location for further processing. In one example, clips 54 in indexing tray 59 would each be individually analyzed to obtain biochemical, genetic, or phenotypic information of interest. In one example, this process could be used as a part of a plant advancement experiment where genetic or phenotypic traits of interest are to be identified to decide whether corresponding cut seed 60 has commercially valuable or desirable genetic or phenotypic traits. If so, the cut seed is needed for continued use in the plant advancement experiment. The cut seed 60 corresponding to the selected clip 54 can be easily and quickly identified by its corresponding index position in index tray 63 and can be shipped to an experimental growing location where it can be planted. As previously mentioned, system 10 is designed to have a substantially high probability that cut seed 60 will germinate at the growing location.

Bar codes could be used and created for each index tray 59 and 63 so that information about the contents of each can be recorded and stored and easily retrieved by scanning the bar codes.

B. EMBODIMENT 2

FIG. 1C

As can be appreciated, the basic idea of magnetic positioning, orientation and, laser cutting can be accomplished in a variety of different ways with a variety of different components and methodologies. FIG. 1C shows an alternative embodiment to that of FIG. 1A. A similar buffer wheel 14 with individual receivers 18 rotated by a motor 17 with shaft 16 is shown. Additionally, a stationary disc 21, having a single opening above chute 22, holds seed in each well 18 of rotating buffer wheel 14 except for the well directly over the opening in disc 21 in alignment with chute 22. In this manner, individual seed 3 is dropped, one at a time and at spaced apart intervals.

The alternative embodiment of FIG. 1C mounts magnets 34 in through-holes in the rim of wheel 72 (e.g. by interference fit) such that a surface of each magnet 34 is directly exposed to the seed. Empirical testing can determine the precise desired magnet for a given embodiment.

In FIG. 1C, a vertically positioned wheel 72 has magnets 34 at spaced apart positions as shown. As wheel 72 turns by chute 22, singulated seeds are deposited in correspondence with the location of each magnet 34. Seeds 3 have crowns painted with iron-based paint. Each seed 3 would thus be both automatically positioned and oriented so that its crown is in abutment with the corresponding magnet 34. Thus, the tip cap is extended outwardly.

The receiver locations 74 along wheel 72 (corresponding with locations of magnets 34) would turn in a counter-clockwise fashion past laser beam 52 of laser 50. Cut seed 60 would serially drop by gravity into seed collection funnel 62. Seed clips 54 would follow around and be serially knocked off the exterior of wheel 72 by scraper 56 and fall into sample collection funnel 58.

In a similar manner to that of the system of FIG. 1A, this singulates seeds, presents them in a consistent position and orientation relative to a laser beam, and allows a relatively precise ability to cut off a portion of each seed, collect clips 54 for use in procedures such as biochemical, genetic, or phenotypic analysis, and collect the cut seeds for possible planting.

C. Options and Alternatives Regarding Embodiments 1 and 2

As can be appreciated, magnetic orientation and/or laser cutting can take various forms and embodiments. Variations obvious to those skilled in the art will be included within this description. The timing of the components can be coordinated by empirical testing. The amount of sample from each seed can be adjusted by adjustment of the laser beam.

Substances that can be attracted by magnets could be applied in different ways to the seed. A possible example is to powder coat a portion of the seed with a mixture that includes highly magnetically active material that would be attracted to a magnet. Another such example is to use a fine spray glue to coat seeds, or if the plant structure on which the seeds are found is appropriate, such structures (i.e. corn cobs) could be dipped into a glue "bath" allowing the outer surfaces of the seeds to be coated with glue. The seeds with wet glue on them can then be brought into contact with particles, such as ferrous, magnetite or hematite particles, which would be attracted to magnets. Additionally, electrostatic substances could be used to charge the surfaces of seeds in order to have better adherence of the substances to the seed. One of skill in the art will recognize that various such methods could be used to obtain the desired result of having the seed partially coated or fully coated with an electrostatic substance.

It may not be necessary to remove the iron-based paint from the sample 54 or cut seed 60. However, it could be done. It could be physically removed (e.g. by abrasion) or chemically removed. A number of paint removing methods are known. The method selected would be based on the intended use of the sample 54 or cut seed 60.

Alternatively, in some cases instead of a substance applied to the object, an independent component could be mounted to the object, where the independent component has a characteristic that can be attracted. For example, a small magnetically active piece or sheet could be adhered or otherwise attached to a pre-determined position on an object related to a desired orientation relative to a magnet. The piece or sheet (the added component to the object) can be permanently mounted to the object. Alternatively it could be temporarily or removably mounted to the object. An example might be a small sheet of magnetically active metal with a releasable adhesive on one side (like used with Post-It™ notes). This would allow the component (the adhesive-backed metal sheet) to be added to each object at a selected position to attract the object at that position to a magnet for orientation. The sheet can then be removed at a later time, if desired.

Placement of the substance or component that is attractable is normally straight forward. In the case of magnetic attraction, the substance or component will normally be pulled into abutment with its corresponding magnet. Therefore, the opposite side of the object will be distal from the magnet.

Additionally, electromagnets might be used instead of permanent magnets. The magnetic field could be turned on to hold, position, and orient the seed for cutting by the laser beam, but then turned off to drop the magnetically attracted part by gravity.

Similar object collection to that of FIGS. 1A and B could be used, or other methods are possible.

The context of these specific examples is with respect to handling and orienting kernels of corn. It is to be understood, however, that this example is only intended to illustrate one application of the invention. The invention can be utilized for handling other objects. The range of sizes can vary as well as the nature of the object. Analogous applications will be obvious from this example and variations obvious to those skilled in the art will be included.

D. EMBODIMENT 3

FIGS. 2A-C

Figure 2A:
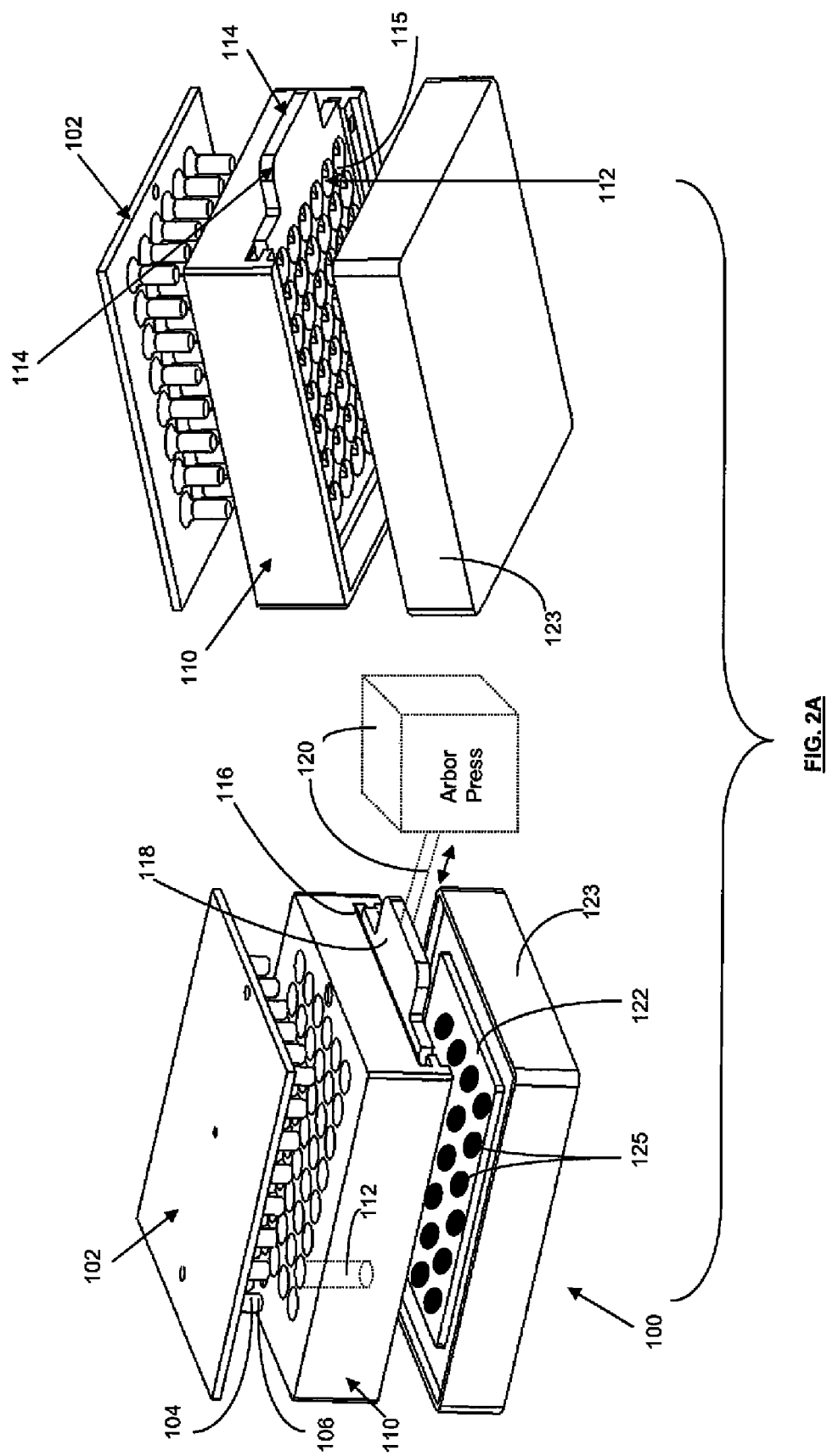
FIG. 2A is an illustration of an exemplary embodiment according to another aspect of the present invention which magnetically positions and orients a plurality of objects, here seed, to allow an operation to be performed concurrently on the objects, here simultaneous chopping off and collection of a portion of each seed.

Magnetic orientation is also used in system 100 of FIG. 2A. Magnet assembly 102 includes a base plate and forty-eight posts 104 extending downwardly from the base plate. A magnet 106 is positioned at or near the distal end of each post 104.

Posts 104 of magnet assembly 102 are inserted into complementary through-holes 112 in cutting assembly 110. The cutting assembly box or housing slideably retains cutting blade 114 in slot 116. Cutting blade has forty-eight openings 115 corresponding in position and spacing to the forty-eight through-holes 112, but the perimeter of each opening 115 is formed, sharpened, or otherwise configured to include a relatively sharp edge.

The combination of the magnet assembly 102 and the cutting assembly 110 is simultaneously lowered into seed box 108 (see FIG. 2C) filled with a mass of singulated seed 3, each with its crown painted with iron-based paint, as previously described (or otherwise a substance or component applied to the crown of each seed that is attracted to a magnet 106). Each magnet 106 would ideally pick up and automatically position and orient a seed 3 so that its crown is in abutment with magnet 106 and its tip cap extends outwardly and distally.

Base 123 includes on its upper side foam pad 122 to secure seeds for cutting. There could be small rings or other similar retainers in correspondence with through-holes 112 when the cutting assembly 110 is positioned on top of base 123 and are used to secure seeds for cutting.

Ear corn 1 is pre-coated with iron-based paint. After the paint is dry, ear 1 is shelled and put into a bin (see FIG. 2C).

The combination of the magnet assembly 102 and the cutting assembly 110 is simultaneously lowered into the bin of seed 3 (each with its crown covered by iron-based paint) to singulate seed 3, one to each post 104 by the attraction of the iron-based paint to a magnet 106 in each post 104.

Each seed 3 is automatically oriented crown-to-magnet because of the iron-based paint on the crown of seed 3. The tip cap of each seed 3 extends distally.

Magnet assembly 102 and cutting assembly 110 are placed on top of base 123 so that through-holes 112 are in correspondence with rings 125 on foam pad 122 of base 123. Blade 114 is located in a position such that its openings 115 are in correspondence with through-holes 112. The magnet assembly 102 and the cutting assembly 110 position the oriented seed 3 such that the tip cap is in abutment with, and slightly compressed against, foam pad 122, but the plane of the cutting edges of openings 115 of blade 114 are aligned just below the crowns of seed 3.

A clamp (e.g. see FIGS. 2B and 2C for examples) secures the combination of base 123, cutting assembly 110, and magnet assembly 102 together. Seed 3 would therefore be oriented by magnets 106, and the structure of the combination would hold seed 3 in that position.

Blade 114 would then be slid in the appropriate direction in slot 116 to move cutting edges of openings 115 into and through each seed 3 to sever a portion of the crown of each seed 3. One example of operation of cutting by blade 114 is shown at FIG. 2C. The combination could be turned on its side, as shown. An arbor press could be operatively connected to handle 118 of blade 114 and operated to push or pull blade 114 to cut seed 3.

After cutting with blade 114 the magnet assembly 102 and cutting assembly 110 are inverted, the clamps are released, and the base 123 is removed (e.g. see FIG. 2A). The cut seed 60 are located in the wells of the blade 114 and are separated from the seed clips or samples 34 as a result of the blade 114 moving sideways during the cutting procedure. The magnet assembly 102 and cutting assembly 110 can then be inverted again over a 48-well tray to collect and index the cut seed 60.

Withdrawal of the magnet assembly 102 from cutting assembly 110 releases the magnetic attraction imposed on the seed clips or samples 34. In this embodiment, the seeds with the magnetically active paint on them are never directly bound to the magnets of the magnet assembly 102. At the bottom of each well in the cutting assembly 110 there is a thin $1/16''$ layer of plastic upon which the magnets rest. The layer is thin enough that the magnetism still permeates through the plastic and attracts the iron-based paint covered seed. When the magnet assembly 102 is lifted the seed chips are released because the plastic prevents them from going with the magnet assembly. In addition the movement of blade 114 back to its original position exposes the seed clips or samples 34. The samples 34 are deposited into a corresponding well of a forty eight well index tray.

Similar to what has been previously discussed, the seed clips or samples 34 can be processed by known-in-the-art processes to derive biochemical, genetic, or phenotypic information about seed 3. The biochemical, genetic, or phenotypic information can be used by plant scientists to select which seed is to be further used in a plant advancement experiment. The cut seed 60 that corresponds with the selected seed clip 34 (by virtue of matching its position in the cut seed index tray with the position of the selected clip or sample in the sample index tray), can then be transported or shipped to the appropriate growing location and planted and grown for further use in the experiment.

E. EMBODIMENT 4

FIG. 2B

Figure 2B:
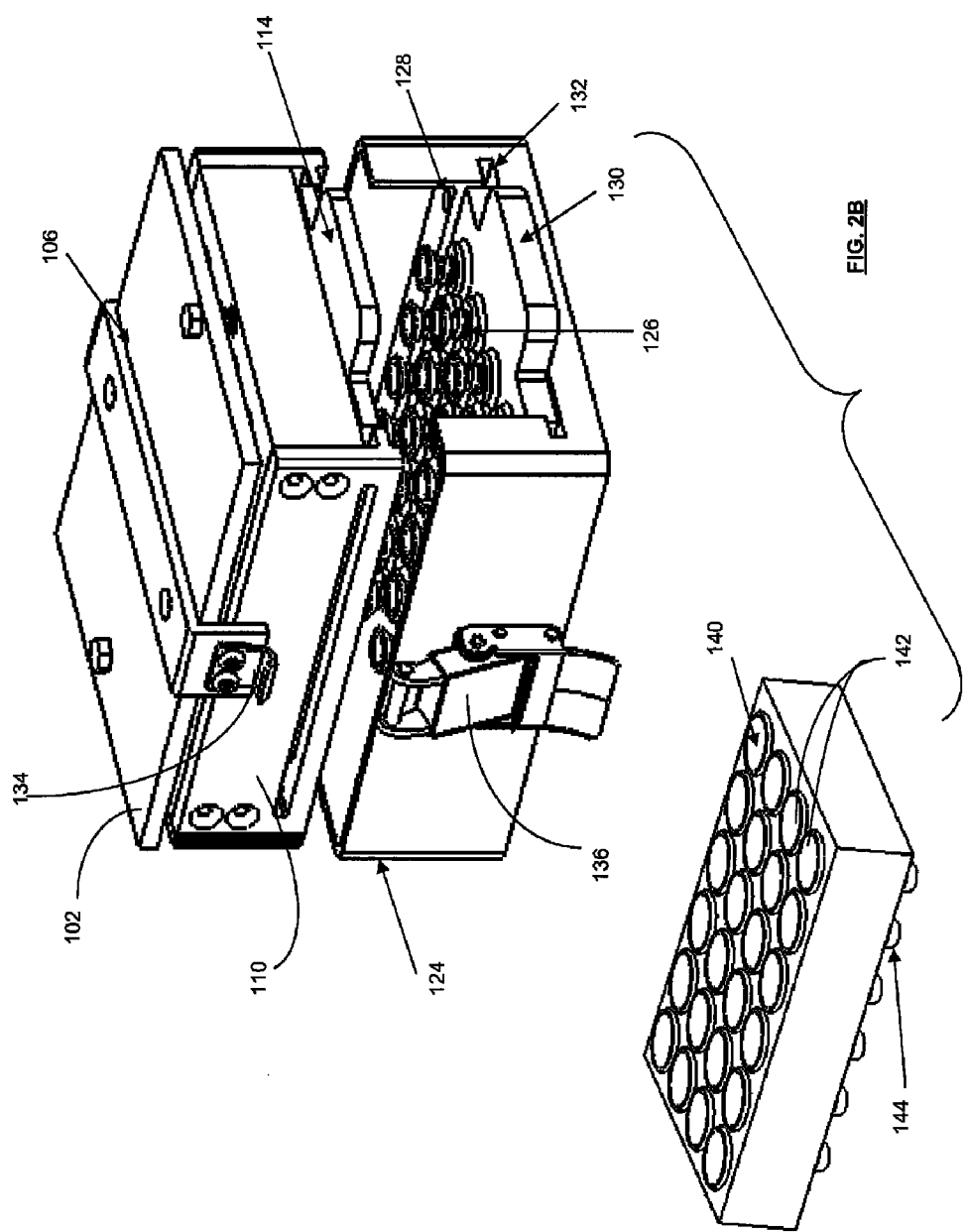
FIG. 2B is an alternative embodiment according to similar principles to the embodiment of FIG. 2A.
Figure 2C:
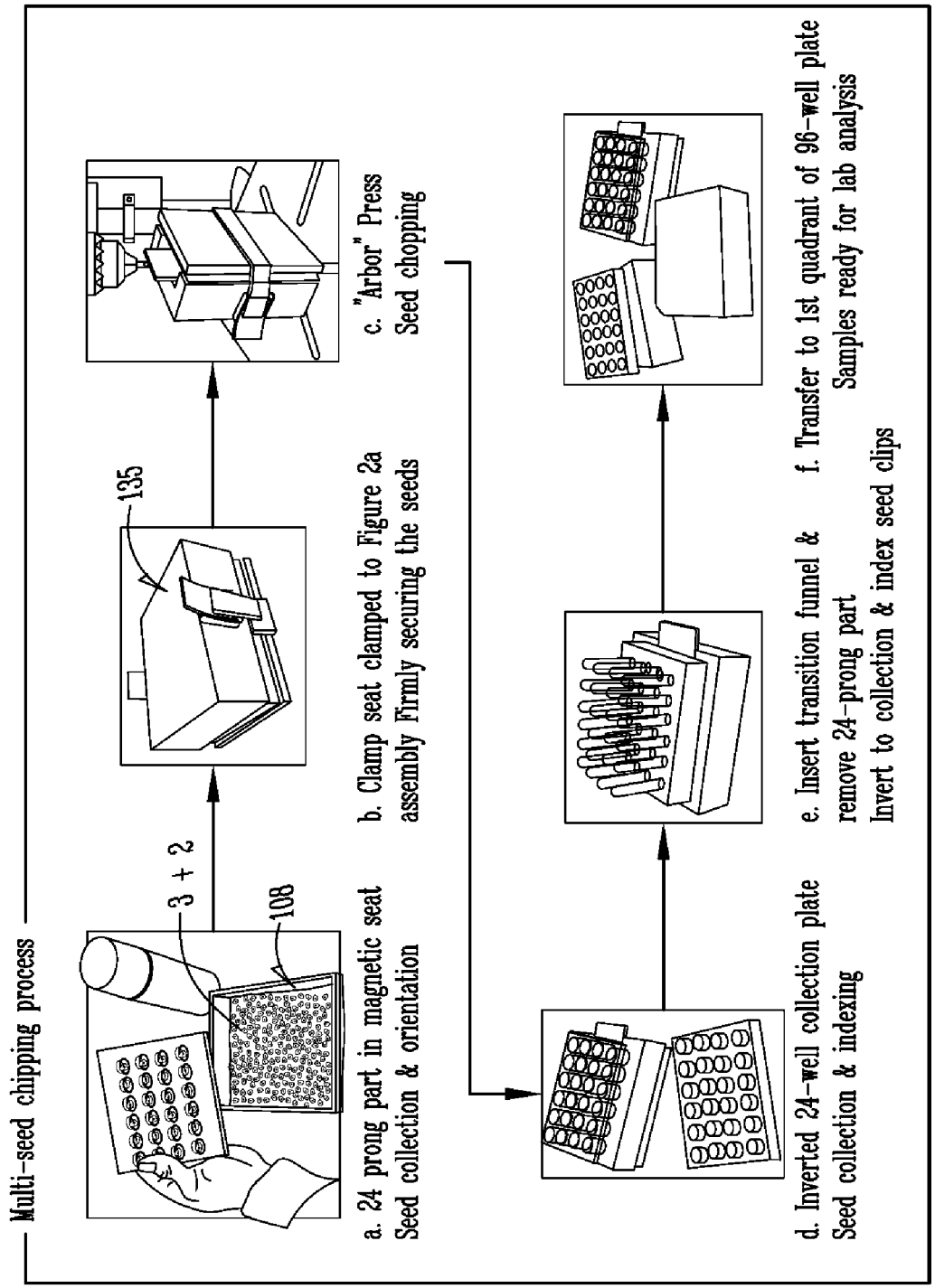
FIG. 2C is an illustration of a method of using the embodiment of FIG. 2B.

FIG. 2B illustrates a similar embodiment to that of FIG. 2A with the following notable differences.

The magnet assembly has twenty-four magnetic posts instead of forty-eight Instead of a foam pad to help hold seed 3 while cutting with blade 114, spring-loaded posts 128 are used. Posts 128 are mounted to a plate 130 that can be inserted into and removed from base 124 through slot 132. The twenty-four spring-loaded posts 128 are biased outwardly by springs, but can be depressed with sufficient force against their distal cup-shaped or funnel-shaped ends.

The cut seed 60 would be collected similarly to that described in the previous embodiment.

Note that FIG. 2B shows an optional 24-well funnel 140, with twenty-four wells 142 on top, each of which terminates in a bullet tube 144 at their bottom. When the combination of FIG. 2B is unclamped and separated after cutting and collection of cut seed 60, funnel 140 can be positioned over one quadrant of a conventional ninety-six well sample plate. Seed clippings 34 are released from the magnet assembly as described in the previous embodiment, directed into the funnel 140, and collected into separate wells of one quadrant of the ninety-six well sample plate.

F. Options and Alternatives Regarding Embodiments 3 and 4

Variations obvious to those skilled in the art will be included within this description. The size and configuration of components can be selected according to need and desire.

Note that FIG. 2C illustrates an optional sample collection method. A set of bullet tubes can be held in corresponding locations to the twenty-four positions of the funnel 140. The seed clippings 34 are first collected in a bullet tube instead of collecting them directly into a standard ninety-six well sample plate. The twenty-four bullet tubes can be inverted and moved into one quadrant of the ninety-six well sample plate (see pictures "e." and "f." of FIG. 2C.) The cutting process could be repeated three more times to fill the other three quadrants of the ninety-six well sample plate. Once full, biochemical, genetic, or phenotypic testing could proceed for ninety-six samples. The cut seed 60 corresponding to each of the ninety-six samples could be collected and indexed with another ninety-six well plate, or with four twenty-four well plates, as shown in picture "d." of FIG. 2C.

It can therefore be seen that the foregoing example allows sorting discrete objects into predetermined spatial positions. In this example it also automatically orients each object in a generally uniform orientation relative to each position.

As can be appreciated, this methodology could be applied to objects other than seed or could be applied to seed that does not have a carrier such as a cob. One example would be soybean seed. The paint could either be applied to a specific portion of each object to promote consistent automatic orientation.

These examples are illustrated relative to the handling of corn seed. It would be advantageous to be able to automatically position individual kernels in a specific orientation. Doing so would allow for such things as being able to cut off the crown of the kernel or take a small tissue sample from a known location automatically. In many state-of-the-art plant breeding experiments, this is done kernel by kernel manually. The amount of labor resources is substantial, particularly when applied to substantial amounts of seed and in a limited time period. Throughput is limited because of the lack of being able to effectively automate these steps.

G. EMBODIMENT 5

The example of FIG. 1 can be applied analogously to objects other than seed. In this embodiment, the basic method and apparatus of FIG. 1A could be used to position and orient in a consistent, pre-determined manner a plurality of non-seed objects. Magnetically active paint would be applied to a consistent location on each object. The objects would be attracted, one each, to individual magnets 34 has they sequentially pass by the singulator (e.g. tube 15 and buffer wheel 14 or analogous mechanism(s)). The objects would be oriented in a consistent manner relative to each magnet 34 on conveyor belt 30.

This would allow a further operation to be performed on each object. An example would be cutting or etching with a laser 50, as illustrated in FIG. 1A. But any of a number of alternative operations could be performed on the oriented objects.

In this example, instead of seed, objects 3 could be metal screws having a head and a threaded shaft. The metal of the screws could be of substantial magnetic activity so that any part of the screw would be attracted to a sufficiently powerful magnet. Thus, in this example, the substance or component which is attractable is inherent in or an original part of the object, as opposed to being added to the object (such as with paint).

A mechanism could feed the screws to buffer wheel 14 one-at-a-time and, for example, head-down, so that each screw would be attracted to a magnet 34 head-down with the distal end of the threaded shaft extending away from the head and magnet. A variety of feeding mechanisms for industrial parts are commercially available to do so (many use vibration and surfaces to move and preliminarily orient the parts as they feed in).

Thus, such a system would provide an efficient, relatively high throughput way to orient each screw in a generally consistent orientation relative to its magnet. This would allow, for example, the screws to be serially conveyed by conveyor 30 to a station or location where another operation could be performed.

An example of another operation would be an assembly step. Each screw could be brought into proximity to a part or sub-assembly in the specific distal-end-up orientation. Automated machinery could engage the head of the screw and screw it into the part or subassembly to complete a step in an assembly process. The next screw could then be moved into position to another location on the same sub-assembly or to another sub-assembly, and the screw could be driven into place. This could repeat as necessary or as desired.

An alternative operation for screws could be that a washer, nut, or coating could be applied to the threaded shaft.

An alternative operation would be that some type of inspection or quality control operation could be performed on each screw. An example would be a machine-vision based system to analysis the threaded shaft. One example would be to analyze if the threads are properly formed. Another would be to analyze length of the shaft. Other inspection operations are possible.

This method could also work for screws that are not inherently magnetically active, or have insufficient magnetic activity to be oriented by magnets. Like with earlier embodiments, a magnetically active substance or component (e.g. magnetically permeable or active paint) could be applied to just the heads of the screws. They would then be attracted to and automatically positioned head-down on the magnets.

H. EMBODIMENT 6

The example of FIG. 1 can be applied analogously to objects other than seed. In this embodiment, the basic method and apparatus of FIG. 1A could be used to position and orient in a consistent, pre-determined manner a plurality of non-seed objects. Magnetically active paint would be applied to a consistent location on each object. The objects would be attracted, one each, to individual magnets 34 has they sequentially pass by the singulator (tube 15 and buffer wheel 14). The objects would be oriented in a consistent manner relative to each magnet 34 on conveyor belt 30. This would allow a further operation to be performed on each object.

In this example, instead of seed or screws, objects 3 could be non-metal pieces (e.g. computer key-board keys) that require application of a letter or number on one side. Similar to Embodiment 1, the opposite side of the plastic keys would be painted with magnetically active paint so that each would be attracted at that metal-coated base side to a magnet with the top exposed. Instead of laser cutter, a mechanism could apply a desired letter or number or symbol to the top of the keys. It could be a printer that moves to and abuts the top of the key and marks the number or letter on the key. Or it could be some type of spray or ink jet device that merely moves into proximity of the top of the key. The metal paint on the base of the plastic keys would be of substantial magnetic activity so that the base would be sufficiently attracted to a sufficiently powerful magnet. Thus, in this example, the substance or component which is attractable is added to the plastic keys and has no function for the key when in final form.

I. EMBODIMENT 7

In this example, objects 3 could be non-metal pieces (e.g. small wooden figurines having a base and a head) that require a certain orientation for packaging. Similar to Embodiment 1, the base side of the wooden figurines could be painted with magnetically active paint so that each would be attracted at that metal-coated base side to a magnet. Instead of laser cutter, a automated mechanism could apply a packaging to or around the figurine. The metal paint on the base of the figurine would be of substantial magnetic activity so that the base would be sufficiently attracted to a sufficiently powerful magnet. Thus, in this example, the substance or component which is attractable is added to the objects (the wooden figurines) and may have no function for the figure when in final form.

Alternatively, the metal paint might have a function. It might allow the figurine to be removable mounted to a magnet in a stand for the figurine.

J. Options, Alternatives, and Variations

It will be appreciated that the present invention can take various configurations and applications. The foregoing examples are exemplary only.

For example, iron-based paint is an example of a substance or addition (ferro-magnetism) that can be utilized to automatically attract or position the object. Other things could be utilized. An example is an adhesive that could be applied at least to a portion of the object and that portion could be dipped into iron particles.

The types of objects with which the invention can be used can also vary. Applications to a variety of objects are described above. Other objects and applications are possible. For example, it could be used to position and orient other metal or non-metal hardware so that each is in position to be applied in a manufacturing or assembly process. Another application would be to position and orient electrical or electronic components in preparation for soldering or mounting on a circuit board. Other manufacturing or assembly processes are, of course possible. The present invention is applicable to many situations where positioning in a desired pattern and/or a desired orientation is required.

What is claimed is:

1. A method of automatic orientation of an object comprising:
   a. adding a substance or component to a pre-determined location on the object, the pre-determined location relating to a pre-determined orientation of the object, the substance or component having a characteristic that can be utilized to automatically attract the substance or component; and
   b. utilizing the characteristic to automatically position the object in the pre-determined orientation.

2. The method of claim 1 wherein the substance or component comprises a magnetically active substance or component.

3. The method of claim 2 wherein the magnetically active substance or component comprises iron-based paint or particles.

4. The method of claim 1 where the magnetically active substance or component is applied to the object to automatically orient the object relative to a reference position.

5. The method of claim 4 wherein the reference position is correlated to a further operation relative to the object.

6. The method of claim 1 further comprising applying steps a. and b. to at least a second object.

7. The method of claim 6 further comprising automatically attracting each object serially.

8. The method of claim 6 further comprising automatically attracting the objects concurrently.

9. The method of claim 1 wherein the positioning is used in a manufacturing or assembly process.

10. The method of claim 9 wherein the object comprises one of a part, a seed, or a package.

11. An apparatus for automatic orientation of an object, said apparatus comprising:
    a. an attracting device configured to generate an attraction force to attract an object that includes or is adapted to include a substance or component positioned on a pre-determined location of the object and having a characteristic that is automatically attracted by the attraction force, the pre-determined location on the object related to a pre-determined orientation of the object; and
    b. a translating device adapted to move said object into proximity of the attracting device or vise versa;
    wherein said object can be automatically oriented in the pre-determined orientation relative to the attracting device.

12. The apparatus of claim 11 wherein the attracting device comprises a magnet adapted to generate a magnetic field which can attract a magnetically active substance or component.

13. The apparatus of claim 12 wherein the magnet is one of a permanent magnet or electromagnet.

14. The apparatus of claim 12 wherein the magnetically active substance or component comprises magnetically active paint or particles.

15. The apparatus of claim 14 wherein the magnetically active particles are held on the object by an adhesive.

16. The apparatus of claim 11 wherein the object comprises one of a part, a seed, or a package.

17. The apparatus of claim 11 wherein the translating device to move the object comprises a conveying system.

18. The apparatus of claim 17 wherein the conveying system comprises a conveyor belt with a plurality of attracting devices adapted to each attract an object.

19. The apparatus of claim 17 wherein the conveying system comprises a wheel with a plurality of attracting devices adapted to each attract an object.

20. The apparatus of claim 11 further comprising a means to separate the object from the attracting device.

21. An apparatus for handling and automatic orientation of one or more objects, said apparatus comprising:

a. a conveying mechanism including a plurality of attracting devices each adapted to generate an attraction force to attract and move, at least between first and second locations, one or more objects each of which includes or is adapted to include a substance or component positioned on a pre-determined location of the object and having a characteristic that is automatically attracted by the attraction force, the pre-determined location being relatively consistent with respect to each object and being related to a pre-determined orientation of each object, and b. a feed mechanism adapted to serially present said one or more objects to the conveying mechanism;

wherein each of said one or more objects is automatically and relatively consistently positioned and oriented in the pre-determined orientation when moved by the conveying mechanism.

22. An apparatus for handling and automatic orientation of one or more objects, said apparatus comprising:

a. a conveying mechanism including a plurality of attracting devices each adapted to generate an attraction force to attract one or more objects each of which includes or is adapted to include a substance or component positioned on a pre-determined location of the object and having a characteristic that is automatically attracted by the attraction force, the pre-determined location being relatively consistent with respect to each object and being related to a pre-determined orientation of each object, the plurality of attracting devices being further adapted to move said one or more objects at least between first and second locations;

b. a feed mechanism adapted to serially present said one or more objects to the conveying mechanism; and c. an operation station adapted to perform a function on any or all of said one or more objects;

wherein each of said one or more objects is automatically and relatively consistently positioned and oriented in the pre-determined orientation when moved by the conveying mechanism to the operation station.

23. The apparatus of claim 22 wherein the operation station comprises a tool, a cutting device, an assembly system, a packaging system, a robot, or an inspection system.

24. An apparatus for automatic orientation of one or more objects, said apparatus comprising:

a. an orientation mechanism including a plurality of attracting devices each adapted to generate an attraction force to attract one or more objects each of which includes or is adapted to include a substance or component positioned on a pre-determined location of the object and having a characteristic that is automatically attracted by the attraction force, the pre-determined location being relatively consistent with respect to each object and being related to a pre-determined orientation of each object;

wherein each of the said one or more objects is automatically, concurrently, and relatively consistently positioned and oriented in the pre-determined orientation when attracted to the orientation mechanism.

25. The apparatus of claim 22 wherein the substance or component comprises a magnetically active substance or component and the attraction devices comprise magnets adapted to generate a magnetic attraction force.

26. The method of claim 1, wherein the object comprises a corn kernel defining a crown and a tip cap opposite the crown, and wherein the substance or component is added to the crown of the corn kernel.

27. The apparatus of claim 11, wherein the object comprises a corn kernel defining a crown and a tip cap opposite the crown, and wherein the substance or component is included or adapted to be included on the crown of the corn kernel.

28. The apparatus of claim 21, wherein the one or more objects comprise one or more corn kernels each defining a crown and a tip cap opposite the crown, and wherein the substance or component is included or adapted to be included on the crown of each corn kernel.

29. The apparatus of claim 22, wherein the one or more objects comprise one or more corn kernels each defining a crown and a tip cap opposite the crown, and wherein the substance or component is included or adapted to be included on the crown of each corn kernel.

30. The apparatus of claim 24, wherein the one or more objects comprise one or more corn kernels each defining a crown and a tip cap opposite the crown, and wherein the substance or component is included or adapted to be included on the crown of each corn kernel.

* * * * *